(12) United States Patent
Simonet et al.

(10) Patent No.: US 7,879,113 B2
(45) Date of Patent: Feb. 1, 2011

(54) COMPOSITION COMPRISING AT LEAST ONE FATTY SUBSTANCE AND AT LEAST ONE SILICATE, DYEING OR LIGHTENING PROCESS USING IT AND DEVICES OR KITS THEREFOR

(75) Inventors: Frédéric Simonet, Clichy (FR); Luc Nicolas-Morgantini, Rully (FR); Aurélie Lafuma, Paris (FR); Marie-Pascale Audousset, Asnieres (FR); Philippe Rapold, Paris (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/642,489

(22) Filed: Dec. 18, 2009

(65) Prior Publication Data

US 2010/0175202 A1  Jul. 15, 2010

Related U.S. Application Data

(60) Provisional application No. 61/151,607, filed on Feb. 11, 2009.

(30) Foreign Application Priority Data

Dec. 19, 2008  (FR) .................................. 08 58889

(51) Int. Cl.
*A61Q 5/10* (2006.01)
(52) U.S. Cl. ........................ 8/405; 8/406; 8/408; 8/435; 8/455; 8/632; 8/111
(58) Field of Classification Search .................. 8/405, 8/406, 408, 435, 455, 632, 111
See application file for complete search history.

(56) References Cited

U.S. PATENT DOCUMENTS

| | | | |
|---|---|---|---|
| 3,100,739 A | 8/1963 | Kaiser et al. | |
| 3,369,970 A | 2/1968 | McLaughlin et al. | |
| 3,629,330 A | 12/1971 | Brody et al. | |
| 3,861,868 A | 1/1975 | Milbrada | |
| 4,138,478 A | 2/1979 | Reese et al. | |
| 4,170,637 A | 10/1979 | Pum | |
| 4,226,851 A | 10/1980 | Sompayrac | |
| 4,357,141 A | 11/1982 | Grollier et al. | |
| 4,366,099 A | 12/1982 | Gaetani et al. | |
| 4,488,564 A | 12/1984 | Grollier et al. | |
| 4,725,282 A | 2/1988 | Hoch et al. | |
| 5,021,066 A | 6/1991 | Aeby et al. | |
| 5,259,849 A | 11/1993 | Grollier et al. | |
| 5,364,414 A | 11/1994 | Lang et al. | |
| 5,817,155 A | 10/1998 | Yasuda et al. | |
| 6,010,541 A | 1/2000 | De La Mettrie | |
| 6,129,770 A | 10/2000 | Deutz et al. | |
| 6,156,713 A | 12/2000 | Chopra et al. | |
| 6,165,444 A | 12/2000 | Dubief et al. | |
| 6,190,421 B1 | 2/2001 | Rondeau et al. | |
| 6,206,935 B1 | 3/2001 | Onitsuka et al. | |
| 6,238,653 B1 | 5/2001 | Narasimhan et al. | |
| 6,260,556 B1 | 7/2001 | Legrand et al. | |
| 6,277,154 B1 | 8/2001 | Lorenz | |
| 6,277,155 B1 | 8/2001 | De La Mettrie et al. | |
| 6,365,136 B1 | 4/2002 | Lauscher et al. | |
| 6,423,100 B1 | 7/2002 | Lang et al. | |
| 6,447,552 B1 | 9/2002 | Golinski | |
| 6,660,045 B1 | 12/2003 | Hoeffkes et al. | |
| 6,695,887 B2 | 2/2004 | Cottard et al. | |
| 6,800,098 B1 | 10/2004 | Allard et al. | |
| 7,135,046 B2 | 11/2006 | Audousset | |
| 7,153,331 B2 | 12/2006 | Desenne et al. | |
| 7,217,298 B2 | 5/2007 | Legrand et al. | |
| 7,285,137 B2 | 10/2007 | Vidal et al. | |
| 7,442,215 B2 | 10/2008 | Audousset et al. | |
| 7,458,993 B2 | 12/2008 | Cottard et al. | |
| 7,494,513 B2 | 2/2009 | Kravtchenko et al. | |
| 7,575,605 B2 | 8/2009 | Legrand | |
| 7,651,533 B2 | 1/2010 | Legrand | |
| 7,651,536 B2 | 1/2010 | Cottard et al. | |

(Continued)

FOREIGN PATENT DOCUMENTS

| | | |
|---|---|---|
| CA | 1 268 421 | 5/1990 |
| CA | 2 573 567 | 3/2006 |
| CH | 507 713 | 7/1971 |
| DE | 20 05 076 | 8/1970 |
| DE | 38 14 356 | 9/1988 |

(Continued)

OTHER PUBLICATIONS

French Search Report for FR 08/58889, dated Sep. 30, 2009.
English language Abstract of DE 199 62 869, dated Jun. 28, 2001.
English language Abstract of DE 10 2006 012 575, dated Feb. 8, 2007.
Copending U.S. Appl. No. 12/339,753, filed Dec. 19, 2008.
Copending U.S. Appl. No. 12/339,781, filed Dec. 19, 2008.
Copending U.S. Appl. No. 12/339,820, filed Dec. 19, 2008.
Copending U.S. Appl. No. 12/642,412, filed Dec. 18, 2009.
Copending U.S. Appl. No. 12/642,451, filed Dec. 18, 2009.
Copending U.S. Appl. No. 12/642,468, filed Dec. 18, 2009.
Copending U.S. Appl. No. 12/642,473, filed Dec. 18, 2009.

(Continued)

*Primary Examiner*—Eisa B Elhilo
(74) *Attorney, Agent, or Firm*—Finnegan, Henderson, Farabow, Garrett & Dunner, LLP

(57) ABSTRACT

The present disclosure relates to a composition for dyeing or lightening human keratin fibers, comprising: a cosmetically acceptable medium; at least 25% by weight of at least one fatty substance; from 0.5% to 15% by weight of at least one silicate chosen from smectite, vermiculite, stevensite and chlorite clays; at least one dye chosen from oxidation dyes and direct dyes; at least one basifying agent; and at least one oxidizing agent. The disclosure also relates to a dyeing or lightening process using it. Another aspect of the disclosure is multi-compartment devices or kits for obtaining, after mixing together the compositions of the compartments, just before its application, a composition according to the disclosure.

26 Claims, No Drawings

U.S. PATENT DOCUMENTS

| | | |
|---|---|---|
| 7,766,977 B2 | 8/2010 | Cottard |
| 2003/0190297 A1 | 10/2003 | Narasimhan et al. |
| 2003/0226217 A1 | 12/2003 | Bowes et al. |
| 2004/0103488 A1 | 6/2004 | Yamashita et al. |
| 2004/0105830 A1 | 6/2004 | Boswell et al. |
| 2004/0181883 A1 | 9/2004 | Legrand et al. |
| 2004/0226110 A1 | 11/2004 | LeGrand |
| 2005/0129652 A1 | 6/2005 | Keller et al. |
| 2005/0165705 A1 | 7/2005 | Lauper et al. |
| 2005/0196367 A1 | 9/2005 | Ohta et al. |
| 2006/0042023 A1 | 3/2006 | Machida |
| 2006/0075580 A1 | 4/2006 | Chan et al. |
| 2006/0137111 A1 | 6/2006 | Au et al. |
| 2006/0242773 A1 | 11/2006 | Kravtchenko et al. |
| 2006/0260071 A1 | 11/2006 | Legrand |
| 2006/0265817 A1 | 11/2006 | Legrand |
| 2007/0006397 A1 | 1/2007 | Schmenger et al. |
| 2007/0033743 A1 | 2/2007 | Kravtchenko |
| 2007/0104672 A1 | 5/2007 | DeCoster et al. |
| 2007/0169285 A1 | 7/2007 | Narasimhan et al. |
| 2007/0275927 A1 | 11/2007 | Philippe |
| 2007/0277331 A1 | 12/2007 | Goldstein et al. |
| 2008/0016627 A1 | 1/2008 | Cottard et al. |
| 2008/0071092 A1 | 3/2008 | Vidal et al. |
| 2008/0229512 A1 | 9/2008 | Syed et al. |
| 2008/0256724 A1 | 10/2008 | Bolton et al. |
| 2009/0007347 A1 | 1/2009 | Cottard et al. |
| 2009/0060855 A1 | 3/2009 | Boche et al. |
| 2009/0151086 A1* | 6/2009 | Brun ............................. 8/405 |
| 2009/0151087 A1 | 6/2009 | Mario et al. |
| 2009/0158533 A1 | 6/2009 | Hercouet |
| 2009/0162309 A1 | 6/2009 | Hercouet et al. |
| 2009/0191142 A1 | 7/2009 | Hercouet et al. |

FOREIGN PATENT DOCUMENTS

| | | |
|---|---|---|
| DE | 38 14 685 | 9/1988 |
| DE | 43 09 509 | 9/1994 |
| DE | 195 27 121 | 1/1997 |
| DE | 197 23 538 | 9/1998 |
| DE | 197 12 980 | 10/1998 |
| DE | 197 54 281 | 6/1999 |
| DE | 198 15 338 | 9/1999 |
| DE | 100 08 640 | 8/2000 |
| DE | 199 09 661 | 9/2000 |
| DE | 199 62 869 | 6/2001 |
| DE | 100 28 723 | 12/2001 |
| DE | 100 56 266 | 5/2002 |
| DE | 101 48 571 | 4/2003 |
| DE | 101 48 671 | 4/2003 |
| DE | 20 2005 008 307 | 7/2005 |
| DE | 10 2005 011 459 | 9/2006 |
| DE | 10 2005 032 798 | 1/2007 |
| DE | 10 2006 012 575 | 2/2007 |
| DE | 10 2005 059 647 | 6/2007 |
| DE | 10 2006 020 050 | 10/2007 |
| DE | 10 2006 061 830 | 6/2008 |
| EP | 0 166 100 | 1/1986 |
| EP | 0 424 261 | 4/1991 |
| EP | 0 890 355 | 1/1999 |
| EP | 1 023 891 | 8/2000 |
| EP | 1 142 563 | 10/2001 |
| EP | 1 166 749 | 1/2002 |
| EP | 1 219 285 | 7/2002 |
| EP | 1 291 006 | 3/2003 |
| EP | 1 314 418 | 5/2003 |
| EP | 1 321 132 | 6/2003 |
| EP | 1 374 842 | 6/2004 |
| EP | 1 430 873 | 6/2004 |
| EP | 1 438 951 | 7/2004 |
| EP | 1 486 195 | 12/2004 |
| EP | 1 488 781 | 12/2004 |
| EP | 1 550 656 | 7/2005 |
| EP | 1 568 354 | 8/2005 |
| EP | 1 570 833 | 9/2005 |
| EP | 1 598 052 | 11/2005 |
| EP | 1 449 512 | 8/2006 |
| EP | 1 707 184 | 10/2006 |
| EP | 1 716 839 | 11/2006 |
| EP | 1 716 840 | 11/2006 |
| EP | 1 733 759 | 12/2006 |
| EP | 1 762 222 | 3/2007 |
| EP | 1 792 602 | 6/2007 |
| EP | 1 813 254 | 8/2007 |
| EP | 1 862 198 | 12/2007 |
| EP | 1 870 085 | 12/2007 |
| EP | 1 902 703 | 3/2008 |
| EP | 1 927 377 | 6/2008 |
| EP | 1 944 009 | 7/2008 |
| EP | 2 005 939 | 12/2008 |
| EP | 2 011 474 | 1/2009 |
| EP | 2 018 848 | 1/2009 |
| EP | 2 072 034 | 6/2009 |
| EP | 2 072 035 | 6/2009 |
| EP | 2 072 036 | 6/2009 |
| FR | 1 517 715 | 3/1968 |
| FR | 2 132 214 | 11/1972 |
| FR | 2 402 446 | 4/1979 |
| FR | 2 496 458 | 6/1982 |
| FR | 2 616 324 | 12/1988 |
| FR | 2 769 835 | 4/1999 |
| FR | 2 779 949 | 12/1999 |
| FR | 2 803 196 | 7/2001 |
| FR | 2 842 101 | 1/2004 |
| FR | 2 870 724 | 12/2005 |
| FR | 2 874 323 | 2/2006 |
| FR | 2 892 623 | 5/2007 |
| FR | 2 910 309 | 6/2008 |
| FR | 2 911 499 | 7/2008 |
| FR | 2 912 903 | 8/2008 |
| FR | 2 912 904 | 8/2008 |
| FR | 2 912 906 | 8/2008 |
| FR | 2 915 886 | 11/2008 |
| FR | 2 919 499 | 2/2009 |
| FR | 2 925 304 | 6/2009 |
| FR | 2 925 307 | 6/2009 |
| FR | 2 925 308 | 6/2009 |
| FR | 2 925 309 | 6/2009 |
| FR | 2 925 311 | 6/2009 |
| GB | 1 288 128 | 9/1972 |
| GB | 1 554 331 | 10/1979 |
| GB | 2 065 177 | 6/1981 |
| GB | 2 142 348 | 1/1985 |
| GB | 2 170 830 | 8/1986 |
| GB | 2 188 948 | 10/1987 |
| GB | 2 217 735 | 11/1989 |
| JP | 58-035106 | 3/1983 |
| JP | 59-106413 | 6/1984 |
| JP | 1-165514 | 6/1989 |
| JP | 10-101537 | 4/1998 |
| JP | 2001-233748 | 8/2001 |
| JP | 2001-302471 | 10/2001 |
| JP | 2003-095984 | 4/2003 |
| JP | 2003-238370 | 8/2003 |
| JP | 2004-262886 | 9/2004 |
| JP | 2006-282524 | 10/2006 |
| JP | 2008-74705 | 4/2008 |
| WO | WO 91/11985 | 8/1991 |
| WO | WO 97/01323 | 1/1997 |
| WO | WO 97/04739 | 2/1997 |
| WO | WO 97/12587 | 4/1997 |
| WO | WO 98/03150 | 1/1998 |
| WO | WO 01/28508 | 4/2001 |
| WO | WO 01/41723 | 6/2001 |

| | | |
|---|---|---|
| WO | WO 01/43709 | 6/2001 |
| WO | WO 01/60327 | 8/2001 |
| WO | WO 02/089748 | 11/2002 |
| WO | WO 03/053329 | 7/2003 |
| WO | WO 03/084495 | 10/2003 |
| WO | WO 2005/025525 | 3/2005 |
| WO | WO 2005/055966 | 6/2005 |
| WO | WO 2006/026851 | 3/2006 |
| WO | WO 2007/006418 | 1/2007 |
| WO | WO 2007/096027 | 8/2007 |
| WO | WO 2008/021641 | 2/2008 |
| WO | WO 2008/096497 | 8/2008 |
| WO | WO 2009/080667 | 7/2009 |
| WO | WO 2009/080668 | 7/2009 |
| WO | WO 2009/080669 | 7/2009 |
| WO | WO 2009/080670 | 7/2009 |

OTHER PUBLICATIONS

Copending U.S. Appl. No. 12/642,480, filed Dec. 18, 2009.
Copending U.S. Appl. No. 12/642,492, filed Dec. 18, 2009.
Copending U.S. Appl. No. 12/642,506, filed Dec. 18, 2009.
Copending U.S. Appl. No. 12/642,513, filed Dec. 18, 2009.
Copending U.S. Appl. No. 12/642,531, filed Dec. 18, 2009.
Copending U.S. Appl. No. 12/642,536, filed Dec. 18, 2009.
Copending U.S. Appl. No. 12/642,543, filed Dec. 18, 2009.
Copending U.S. Appl. No. 12/642,551, filed Dec. 18, 2009.
Copending U.S. Appl. No. 12/642,555, filed Dec. 18, 2009.
Copending U.S. Appl. No. 12/642,568, filed Dec. 18, 2009.
Copending U.S. Appl. No. 12/642,575, filed Dec. 18, 2009.
Copending U.S. Appl. No. 12/642,583, filed Dec. 18, 2009.
Copending U.S. Appl. No. 12/642,592, filed Dec. 18, 2009.
Copending U.S. Appl. No. 12/642,593, filed Dec. 18, 2009.
Copending U.S. Appl. No. 12/642,599, filed Dec. 18, 2009.
Copending U.S. Appl. No. 12/642,624, filed Dec. 18, 2009.
Copending U.S. Appl. No. 12/642,637, filed Dec. 18, 2009.
Copending U.S. Appl. No. 12/809,140, filed Jun. 18, 2010.
English language Abstract of DE 10 2005 011 459, dated Sep. 14, 2006.
English language Abstract of DE 10 2005 032 798, dated Jan. 25, 2007.
English language Abstract of DE 10 2005 059 647, dated Jun. 14, 2007.
English language Abstract of DE 10 2006 020 050, dated Oct. 31, 2007.
English language Abstract of DE 10 2006 061 830, dated Jun. 26, 2008.
English language Abstract of DE 100 28 723, dated Dec. 10, 2001.
English language Abstract of DE 100 56 266, dated May 23, 2002.
English language Abstract of DE 101 48 571, dated Apr. 24, 2003.
English language Abstract of DE 101 48 671, dated Apr. 10, 2003.
English language Abstract of DE 195 27 121, dated Jan. 30, 1997.
English language Abstract of DE 197 12 980, dated Oct. 1, 1998.
English language Abstract of DE 197 23 538, dated Sep. 17, 1998.
English language Abstract of DE 20 05 076, (Aug. 1970).
English language Abstract of DE 38 14 356, dated Jan. 2, 1992.
English language Abstract of DE 43 09 509, dated Sep. 19, 1994.
English language Abstract of DE 1 166 749, dated Jan. 22, 2002.
English language Abstract of EP 1 321 132, dated Jun. 25, 2003.
English language Abstract of EP 1 568 354, dated Aug. 31, 2005.
English language Abstract of EP 1 761 840, (Nov. 2006).
English language Abstract of EP 1 862 198, dated Dec. 5, 2007.
English language Abstract of EP 2 005 939, dated Dec. 24, 2008.
English language Abstract of EP 2 018 848, dated Jan. 28, 2009.
English language Abstract of FR 2 616 324, dated Dec. 16, 1988.
English language Abstract of FR 2 779 949, dated Dec. 24, 1999.
English language Abstract of FR 2 842 101, dated Jan. 16, 2004.
English language Abstract of FR 2 870 724, dated Dec. 2, 2005.
English language Abstract of FR 2 910 309, dated Jun. 27, 2008.
English language Abstract of FR 2 911 499, dated Jul. 25, 2008.
English language Abstract of FR 2 912 903, dated Aug. 29, 2008.
English language Abstract of FR 2 912 904, dated Aug. 29, 2008.
English language Abstract of FR 2 912 906, dated Aug. 29, 2008.
English language Abstract of FR 2 915 886, dated Nov. 14, 2008.
English language Abstract of FR 2 919 499, dated Feb. 6, 2009.
English language Abstract of FR 2 925 304, dated Jun. 26, 2009.
English language Abstract of FR 2 925 308, dated Jun. 26, 2009.
English language Abstract of FR 2 925 309, dated Jun. 26, 2009.
English language Abstract of JP 1-165514, dated Jun. 29, 1989.
English language Abstract of JP 2001-233748, dated Aug. 28, 2001.
English language Abstract of JP 2001-302471, dated Oct. 31, 2001.
English language Abstract of JP 2003-095984, dated Apr. 3, 2003.
English language Abstract of JP 2003-238370, dated Aug. 27, 2003.
English language Abstract of JP 2004-262886, dated Sep. 24, 2004.
English language Abstract of JP 2006-282524, dated Oct. 19, 2006.
English language Abstract of JP 2008-074705, dated Apr. 3, 2008.
English language Abstract of JP 58-035106, dated Mar. 1, 1983.
English language Abstract of JP 59-106413, dated Jun. 20, 1984.
English language Abstract of WO 2007/096027, dated Aug. 30, 2007.
English language Abstract of WO 2007/006418, (Jan. 2007).
English language Abstract of WO 2008/096497, (Aug. 2008).
English language Abstract of WO 91/11985, dated Aug. 22, 1991.
English language Abstract of WO 97/04739, dated Feb. 13, 1997.
European Search Report for EP 08 17 2444, dated Apr. 13, 2009.
European Search Report for EP 08 17 2449, dated Apr. 13, 2009.
European Search Report for EP 08 17 2454, dated Apr. 3, 2009.
European Search Report for EP 09 17 9779, dated May 5, 2010.
European Search Report for EP 09 17 9789, dated Feb. 19, 2010.
European Search Report for EP 09 17 9844, dated Apr. 22, 2010.
European Search Report for EP 09 17 9884, dated Feb. 24, 2010.
European Search Report for EP 09 17 9885, dated Feb. 25, 2010.
European Search Report for EP 09 17 9887, dated Feb. 25, 2010.
European Search Report for EP 09 17 9888, dated Mar. 24, 2010.
European Search Report for EP 09 17 9892, dated Apr. 8, 2010.
European Search Report for EP 09 17 9895, dated Feb. 23, 2010.
European Search Report for EP 09 17 9899, dated Mar. 17, 2010.
European Search Report for EP 09 17 9911, dated Apr. 26, 2010.
European Search Report for EP 09 17 9914, dated Mar. 25, 2010.
European Search Report for EP 09 17 9992, dated Mar. 24, 2010.
European Search Report for EP 09 18 0003, dated Feb. 24, 2010.
French Search Report for FR 07/60273, dated Aug. 20, 2008.
French Search Report for FR 07/60274, dated Aug. 20, 2008,.
French Search Report for FR 07/60277, dated Aug. 20, 2008.
French Search Report for FR 07/60278, dated Aug. 20, 2008.
French Search Report for FR 08/07283, dated Sep. 30, 2009.
French Search Report for FR 08/07285, dated Sep. 28, 2009.
French Search Report for FR 08/07286, dated Sep. 24, 2009.
French Search Report for FR 08/07287, dated Oct. 13, 2009.
French Search Report for FR 08/07288, dated Nov. 4, 2009.
French Search Report for FR 08/07290, dated Oct. 14, 2009.
French Search Report for FR 08/07291, dated Oct. 19, 2009.
French Search Report for FR 08/07292, dated Aug. 25, 2009.
French Search Report for FR 08/07294, dated Aug. 19, 2009.
French Search Report for FR 08/07298, dated Nov. 2, 2009.
French Search Report for FR 08/07304, dated Oct. 1, 2009.
French Search Report for FR 08/07306, dated Aug. 13, 2009.
French Search Report for FR 08/07307, dated Aug. 24, 2009.
French Search Report for FR 08/07309, dated Aug. 3, 2009.
French Search Report for FR 08/07310, dated Oct. 2, 2009.
French Search Report for FR 08/07312, dated Oct. 1, 2009.
French Search Report for FR 08/07313, dated Aug. 26, 2009.
French Search Report for FR 08/07314, dated Aug. 27, 2009.
French Search Report for FR 08/07315, dated Nov. 11, 2009.
French Search Report for FR 08/07316, dated Nov. 18, 2009.
French Search Report for FR 08/07319, dated Aug. 3, 2009.
French Search Report for FR 08/07320, dated Sep. 15, 2009.
French Search Report for FR 08/07321, dated Aug. 5, 2009.
French Search Report for FR 08/07322, dated Sep. 24, 2009.
French Search Report for FR 08/07323, dated Sep. 24, 2009.
French Search Report for FR 08/58838, dated Sep. 3, 2009.
French Search Report for FR 08/58840, dated Sep. 30, 2009.
French Search Report for FR 08/58880, dated Sep. 18, 2009.
French Search Report for FR 08/58881, dated Sep. 29, 2009.
French Search Report for FR 08/58886, dated Nov. 3, 2009.
French Search Report for FR 08/58888, dated Nov. 3, 2009.
French Search Report for FR 08/58890, dated Sep. 21, 2009.

French Search Report for FR 08/58891, dated Aug. 24, 2009.
French Search Report for FR 08/58892, dated Sep. 24, 2009.
French Search Report for FR 09/51367, dated Jan. 29, 2010.
French Search Report for FR 09/54264, dated Mar. 5, 2010.
French Search Report for FR 09/56389, dated Jun. 14, 2010.
French Search Report for FR 09/57176, dated Jun. 17, 2010.
International Search Report for PCT/FR2009/052617, dated Mar. 30, 2010.
Notice of Allowance mailed Aug. 10, 2010, in U.S. Appl. No. 12/339,820.
Notice of Allowance mailed Aug. 26, 2010, in U.S. Appl. No. 12/642,624.
Notice of Allowance mailed Aug. 26, 2010, in U.S. Appl. No. 12/642,637.
Notice of Allowance mailed Aug. 27, 2010, in U.S. Appl. No. 12/642,513.
Notice of Allowance mailed in co-pending U.S. Appl. No. 12/339,753, dated Jul. 9, 2010.
Office Action mailed Aug. 11, 2010, in co-pending U.S. Appl. No. 12/642,593.
Office Action mailed Aug. 26, 2010, in co-pending U.S. Appl. No. 12/642,473.
Office Action mailed Feb. 1, 2010, in co-pending U.S. Appl. No. 12/339,753.
Office Action mailed Mar. 15, 2010, in co-pending U.S. Appl. No. 12/339,820.
Office Action mailed Sep. 3, 2010, in co-pending U.S. Appl. No. 12/642,451.
STIC Search Report for U.S. Appl. No. 12/339,820, dated Jan. 21, 2010.

* cited by examiner

COMPOSITION COMPRISING AT LEAST ONE FATTY SUBSTANCE AND AT LEAST ONE SILICATE, DYEING OR LIGHTENING PROCESS USING IT AND DEVICES OR KITS THEREFOR

This application claims benefit of U.S. Provisional Application No. 61/151,607, filed Feb. 11, 2009. This application also claims benefit of priority under 35 U.S.C. §119 to French Patent Application No. 0858889, filed Dec. 19, 2009.

The present disclosure relates to a composition for dyeing or lightening human keratin fibers, comprising, besides at least one oxidizing agent, a high content of fatty substances and at least one silicate. The disclosure also relates to a dyeing or lightening process using it and to multi-compartment devices or kits.

Among the methods for dyeing human keratin fibers, such as the hair, exemplary mention may be made of oxidation dyeing or permanent dyeing. For example, this dyeing method uses at least one oxidation dye, usually at least one oxidation base optionally combined with at least one coupler.

In general, oxidation bases may be chosen from ortho- or para-phenylenediamines, ortho- or para-aminophenols and heterocyclic compounds. These oxidation bases may be colorless or weakly colored compounds, which, when combined with oxidizing products, may give access to colored species.

The shades obtained with these oxidation bases are often varied by combining them with at least one coupler, the at least one coupler being chosen, for example, from aromatic meta-diamines, meta-aminophenols, meta-diphenols and certain heterocyclic compounds, such as indole compounds.

The variety of molecules that may be used as oxidation bases and couplers allows a wide range of colors to be obtained.

It is also possible to add to these compositions direct dyes, which are colored and coloring molecules that have affinity for fibers. The direct dyes generally used may be chosen from nitrobenzene, anthraquinone, nitropyridine, azo, methine, azomethine, xanthene, acridine, azine and triarylmethane direct dyes. The presence of such compounds may enable the obtained coloration to be further enriched with tints or may enable the chromaticity of the obtained coloration to be increased.

Oxidation dyeing processes thus may consist in using with these dye compositions a composition comprising at least one oxidizing agent, such as hydrogen peroxide, under alkaline pH conditions in the vast majority of cases. The role of this oxidizing agent is to reveal the coloration, via an oxidative condensation reaction between the oxidation dyes.

It is desired that the oxidation dye should moreover satisfy at least one of a certain number of requirements. Thus, it should be free of toxicological drawbacks, it should enable shades to be obtained in the desired intensity and/or it should show the resistance to external attacking factors such as light, bad weather, washing, permanent waving, or aspiration and rubbing.

The dyes may also be able to cover grey hair and, finally, they should be as unselective as possible, i.e. they should produce the smallest possible color differences along the same keratin fiber, which generally comprises areas that are differently sensitized (i.e. damaged) from its end to its root.

Many attempts have been made in the field of hair dyeing in order to improve the dyeing properties, for example using adjuvants. However, the choice of these adjuvants is difficult insofar as they should improve the dyeing properties of dye compositions without harming the other properties of these compositions. For example, these adjuvants should not harm the keratin fiber-lightening properties and the dye application properties.

As regards processes for lightening keratin fibers, use may be made of aqueous compositions comprising at least one oxidizing agent, under alkaline pH conditions in the vast majority of cases. The role of this oxidizing agent is to degrade the melanin of the hair, which, depending on the nature of the oxidizing agent present, may lead to more or less pronounced lightening of the fibers.

One of the difficulties arises from the fact that lightening processes are performed under alkaline conditions and that the alkaline agent most commonly used is ammonia. The use of this compound may be frequent, since it not only enables adjustment of the pH to allow activation of the oxidizing agent, but also causes swelling of the fiber, with opening of the scales, which may promote penetration of the oxidizing agent and may increases the efficacy of the reaction. However, this basifying agent is very volatile, which may make it necessary to use it in relatively large amounts to compensate for the losses, the consequence of which is the inconvenience caused by the characteristic odor of this compound.

Accordingly, one aspect of the present disclosure is to obtain compositions for the dyeing, such as the oxidation dyeing of keratin fibers, which do not have at least one of the drawbacks of the prior art.

For example, one of the aims of the present disclosure is to obtain compositions for the dyeing, such as the oxidation dyeing of keratin fibers, with improved dyeing properties, which can achieve the desired lightening and which are easy to mix and to apply, and which may not run but may remain localized at the point of application. The term "improved dyeing properties" is understood to mean an improvement in the power/intensity, chromaticity and/or uniformity of the dyeing result.

Another aspect of the present disclosure is to propose keratin fiber-lightening compositions that do not have at least one of the drawbacks of those used with the existing compositions, these drawbacks being caused by the presence of large amounts of ammonia, and which may remain at least as efficient as regards the lightening and the uniformity of this lightening.

These aims and others may be achieved by the present disclosure, one aspect of which is thus a composition for dyeing or lightening human keratin fibers, comprising, a cosmetically acceptable medium;
at least 25% by weight of at least one fatty substance;
from 0.1% to 15% by weight of at least one silicate chosen from smectite, vermiculite, stevensite and chlorite clays;
at least one dye chosen from oxidation dyes and direct dyes;
at least one basifying agent; and
at least one oxidizing agent.

One aspect of the present disclosure is also a composition for dyeing human keratin fibers, characterized in that it comprises:

a cosmetically acceptable medium;
at least 25% by weight of at least one fatty substances;
from 0.1% to 15% by weight of at least one silicate chosen from smectite, vermiculite, stevensite and chlorite clays;
at least one oxidation dye; and
at least one oxidizing agent.

The disclosure also relates to a process for dyeing human keratin fibers, comprising using the abovementioned composition.

The disclosure furthermore relates to a process for lightening human keratin fibers comprising the abovementioned composition.

Another aspect of the disclosure is a multi-compartment device or kit comprising:

at least one compartment containing a first composition comprising at least one fatty substance; and optionally at least one dye chosen from oxidation dyes and direct dyes; and at least one compartment containing a second composition comprising at least one oxidizing agent;

wherein at least one silicate chosen from smectite, vermiculite, stevensite and chlorite clays is present in at least one of the compositions, for example in the first;

and at least one basifying agent is optionally present in either composition, and in at least one embodiment is present in the first composition;

the compositions of the compartments being intended to be mixed together to give the composition according to the disclosure, just before application to human keratin fibers. Another aspect of the disclosure is a multi-compartment device or kit comprising, at least one compartment containing a first composition comprising at least one fatty substance, at least one oxidation dye and at least one silicate, and at least one compartment containing a second composition comprising at least one oxidizing agent;

the compositions of the compartments being intended to be mixed together to give the composition according to the disclosure, just before application to human keratin fibers.

The disclosure furthermore relates to a multi-compartment device or kit comprising:

at least one compartment containing a first composition comprising at least one fatty substance, at least one compartment containing a second composition comprising at least one dye chosen from oxidation dyes and direct dyes and at least one basifying agent; and at least one compartment containing a third composition comprising at least one oxidizing agent;

wherein at least one silicate chosen from smectite, vermiculite, stevensite and chlorite clays is present in at least one of the compositions, and in at least one embodiment is present in at least the first composition;

the compositions of the compartments being intended to be mixed together to give the composition according to the disclosure, just before application to human keratin fibers.

Further, the disclosure relates to a multi-compartment device or kit comprising, at least one compartment containing a first composition comprising at least one fatty substance, and at least one silicate chosen from smectite, vermiculite, stevensite and chlorite clays;

at least one compartment containing a second composition comprising at least one oxidation dye; and at least one compartment containing a third composition comprising at least one oxidizing agent;

the compositions of the compartments being intended to be mixed together to give the composition according to the disclosure, just before application to human keratin fibers.

Other characteristics and benefits of the disclosure will emerge more clearly on reading the description and the non-limiting examples that follow.

In the present disclosure, unless otherwise indicated, the limits of a range of values are included in that range.

In at least one embodiment, the human keratin fibers treated via the process according to the disclosure are hair.

When the composition according to the disclosure is used for lightening, it does not comprise any direct dye or oxidation dye precursor (bases and couplers) usually used for the dyeing of human keratin fibers, or, if it does comprise any, their total amount does not exceed 0.005% by weight relative to the total weight of the composition. Specifically, at such a content, only the composition would optionally be dyed, i.e. no coloration effect would be observed on the keratin fibers.

In at least one embodiment, the lightening process is performed without oxidation base or coupler or direct dye.

As indicated previously, the dyeing or lightening composition according to the disclosure comprises at least 25% by weight of at least one fatty substance.

The term "fatty substance" means an organic compound that is insoluble in water at ordinary temperature (25° C.) and at atmospheric pressure (760 mmHg) (solubility of less than 5%, such as 1% or such as 0.1%). They have in their structure at least one hydrocarbon-based chain containing at least 6 carbon atoms or a sequence of at least two siloxane groups. In addition, the fatty substances are generally soluble in organic solvents under the same temperature and pressure conditions, for instance chloroform, ethanol, benzene, liquid petroleum jelly or decamethylcyclopentasiloxane.

According to the disclosure, the fatty substances are chosen from compounds that are liquid or pasty at room temperature and at atmospheric pressure.

In at least one embodiment, the at least one fatty substance is chosen from $C_6$-$C_{16}$ lower alkanes, non-silicone oils of animal, plant, mineral or synthetic origin, fatty alcohols, fatty acids, fatty acid esters, fatty alcohol esters, non-silicone waxes and silicones.

For the purposes of the disclosure, the fatty alcohols, fatty esters and fatty acid esters contain at least one linear or branched, saturated or unsaturated hydrocarbon-based group containing 6 to 30 carbon atoms, which is optionally substituted, for example with at least one hydroxyl group (for example from 1 to 4). If they are unsaturated, these compounds may comprise one to three conjugated or non-conjugated carbon-carbon double bonds.

As regards the $C_6$-$C_{16}$ lower alkanes, they may be linear or branched, or possibly cyclic. Non-limiting examples that may be mentioned include hexane, undecane, dodecane, tridecane and isoparaffins such as isohexadecane and isodecane.

As oils of animal, plant, mineral or synthetic origin that may be used in the composition of the disclosure, non-limiting examples that may be mentioned include:

hydrocarbon-based oils of animal origin, such as perhydrosqualene;

triglyceride oils of plant or synthetic origin, such as liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, castor oil, avocado oil, caprylic/capric acid triglycerides, for instance those sold by the company Stéarineries Dubois or those sold under the names MIGLYOL® 810, 812 and 818 by the company Dynamit Nobel, jojoba oil and shea butter oil;

linear or branched hydrocarbons of mineral or synthetic origin, containing more than 16 carbon atoms, such as volatile or non-volatile liquid paraffins, and derivatives thereof, petroleum jelly, liquid petroleum jelly, polydecenes, hydrogenated polyisobutenes such as PARLEAM®; for example liquid paraffins, petroleum jelly, liquid petroleum jelly, polydecenes, hydrogenated polyisobutenes such as PARLEAM®;

fluoro oils, for instance perfluoromethylcyclopentane and perfluoro-1,3-dimethylcyclohexane, sold under the names FLUTEC® PC1 and FLUTEC® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name FORALKYL® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that are suitable for use in the disclosure can be, for example, chosen from linear or branched, saturated or unsaturated alcohols containing from 8 to 30 carbon atoms. Examples that may be mentioned include cetyl alcohol, stearyl alcohol and the mixture thereof (cetylstearyl alcohol), octyldodecanol, 2-butyloctanol, 2-hexyldecanol, 2-undecylpentadecanol, oleyl alcohol and linoleyl alcohol.

The fatty acids that may be used in the context of the disclosure are, in at least one embodiment, chosen from saturated or unsaturated carboxylic acids containing from 6 to 30 carbon atoms, such as from 9 to 30 carbon atoms. In at least one embodiment, they are chosen from myristic acid, palmitic acid, stearic acid, behenic acid, oleic acid, linoleic acid, linolenic acid and isostearic acid.

As regards the fatty acid esters and fatty alcohol esters, which are different from the triglycerides mentioned above, non-limiting mention may be made of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters being greater than or equal to 10.

Among the monoesters, non-limiting mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, and 2-hexyldecyl laurate.

In at least one embodiment, these esters are chosen from esters of $C_4$-$C_{22}$ dicarboxylic and tricarboxylic acids and of $C_1$-$C_{22}$ alcohols and esters of mono-, di- or tricarboxylic acids and of $C_2$-$C_{26}$ di-, tri-, tetra- or pentahydroxy alcohols.

The following may also be mentioned by way of example: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, in at least one embodiment, the ester is chosen from ethyl, isopropyl, myristyl, cetyl or stearyl palmitate, 2-ethylhexyl palmitate, 2-octyldecyl palmitate, alkyl myristates such as isopropyl, butyl, cetyl or 2-octyldodecyl myristate, hexyl stearate, butyl stearate, isobutyl stearate; dioctyl malate, hexyl laurate, 2-hexyldecyl laurate, isononyl isononanoate and cetyl octanoate.

In at least one embodiment, the composition may comprise, as fatty ester, sugar esters and diesters of $C_6$-$C_{30}$ and in at least one embodiment, $C_{12}$-$C_{22}$ fatty acids. As used herein, the term "sugar" means oxygen-bearing hydrocarbon-based compounds containing several alcohol functions, with or without aldehyde or ketone functions, and which contain at least 4 carbon atoms. These sugars may be monosaccharides, oligosaccharides or polysaccharides.

Examples of suitable sugars that may be mentioned include sucrose (or saccharose), glucose, galactose, ribose, fructose, maltose, mannose, arabinose, xylose and lactose, and derivatives thereof, for example alkyl derivatives, such as methyl derivatives, for instance methylglucose.

In at least one embodiment, the sugar esters of fatty acids may be chosen from the group comprising the esters or mixtures of esters of sugars described previously, linear or branched, saturated or unsaturated $C_6$-$C_{30}$ fatty acid esters, such as $C_{12}$-$C_{22}$ fatty acid esters, and mixtures thereof. If they are unsaturated, these compounds may comprise one to three conjugated or non-conjugated carbon-carbon double bonds.

The esters according to this embodiment may also be chosen from mono-, di-, tri-, tetraesters and polyesters, and mixtures thereof.

These esters may be chosen, for example, from oleates, laurates, palmitates, myristates, behenates, cocoates, stearates, linoleates, linolenates, caprates and arachidonates, or mixtures thereof such as, for example, oleo-palmitate, oleo-stearate and palmito-stearate mixed esters.

In at least one embodiment, the esters are chosen from monoesters and diesters, for example from sucrose, glucose or methylglucose mono- or dioleates, stearates, behenates, oleopalmitates, linoleates, linolenates and oleostearates.

An example that may be mentioned is the product sold under the name GLUCATE® DO by the company Amerchol, which is a methylglucose dioleate.

Examples of esters or mixtures of esters of sugar and of fatty acid that may also be mentioned include:
  the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
  the products sold under the name RYOTO SUGAR ESTERS, for example referenced B370 and corresponding to sucrose behenate formed from 20% monoester and 80% di-triester-polyester;
  the sucrose mono-dipalmito-stearate sold by the company Goldschmidt under the name TEGOSOFT® PSE.

The non-silicone wax(es) is(are) chosen, for example, from carnauba wax, candelilla wax, esparto grass wax, paraffin wax, ozokerite, plant waxes, for instance olive wax, rice wax, hydrogenated jojoba wax and the absolute waxes of flowers such as the essential wax of blackcurrant sold by the company Berlin (France), animal waxes, for instance beeswaxes, and modified beeswaxes (cerabellina); other waxes or waxy raw materials that may be used according to the disclosure include, for example, marine waxes such as the product sold by the company Sophim under the reference M82, and waxes of polyethylene or of polyolefins in general.

The silicones that may be used in the cosmetic compositions of the present disclosure are volatile or non-volatile, cyclic, linear or branched silicones, which are unmodified or modified with organic groups, having a viscosity ranging from $5 \times 10^{-6}$ to $2.5$ m$^2$/s at 25° C., for example from $1 \times 10^{-5}$ to $1$ m$^2$/s.

The silicones that may be used in accordance with the disclosure may be in the form of oils, waxes, resins or gums.

In at least one embodiment, the silicone is chosen from polydialkylsiloxanes, and in at least one embodiment is chosen from polydimethylsiloxanes (PDMS), and organomodified polysiloxanes comprising at least one functional group chosen from poly(oxyalkylene) groups, amino groups and alkoxy groups.

The organopolysiloxanes are defined in greater detail in Walter Noll's "Chemistry and Technology of Silicones" (1968) Academic Press. They can be volatile or non-volatile.

When they are volatile, the silicones are, for example, chosen from those having a boiling point of ranging from 60° C. to 260° C., and in at least one embodiment are chosen from:

(i) cyclic polydialkylsiloxanes containing from 3 to 7, such as from 4 to 5 silicon atoms. These include, for example, octamethylcyclotetrasiloxane sold, for example under the name VOLATILE SILICONE® 7207 by Union Carbide or SILBIONE® 70045 V2 by Rhodia, decamethylcyclopentasiloxane sold under the name VOLATILE SILICONE® 7158 by Union Carbide, and SILBIONE® 70045 V5 by Rhodia, and mixtures thereof.

Exemplary mention may also be made of cyclocopolymers of the dimethylsiloxane/methylalkylsiloxane type, such as VOLATILE SILICONE® FZ 3109 sold by the company Union Carbide, of formula:

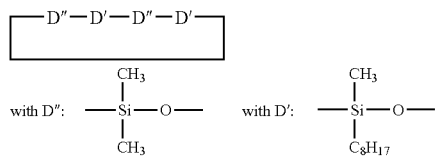

Mention may also be made, for example, of mixtures of cyclic polydialkylsiloxanes with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile polydialkylsiloxanes containing from 2 to 9 silicon atoms and having a viscosity of less than or equal to $5 \times 10^{-6}$ m$^2$/s at 25° C. An example is decamethyltetrasiloxane sold, for example, under the name SH 200 by the company Toray Silicone. Silicones belonging to this category are also described in the article published in Cosmetics and Toiletries, Vol. 91, Jan. 76, pp. 27-32, Todd & Byers "Volatile Silicone Fluids for Cosmetics".

In at least one embodiment, non-volatile polydialkylsiloxanes, polydialkylsiloxane gums and resins, polyorganosiloxanes modified with organofunctional groups above, and mixtures thereof, are used.

These silicones are, in at least one embodiment, chosen from polydialkylsiloxanes, among which mention may be made mainly of polydimethylsiloxanes containing trimethylsilyl end groups. The viscosity of the silicones is measured, for example, at 25° C. according to ASTM standard 445 Appendix C.

Among these polydialkylsiloxanes, exemplary mention may be made, in a nonlimiting manner, of the following commercial products:

the SILBIONE® oils of the 47 and 70 047 series or the MIRASIL® oils sold by Rhodia, for instance the oil 70 047 V 500 000;

the oils of the 200 series from the company Dow Corning, such as DC200 with a viscosity of 60,000 mm$^2$/s;

the VISCASIL® oils from General Electric and certain oils of the SF series (SF 96, SF 18) from General Electric.

Mention may also be made, for example, of polydimethylsiloxanes containing dimethylsilanol end groups known under the name Dimethiconol (CTFA), such as the oils of the 48 series from the company Rhodia.

In this category of polydialkylsiloxanes, exemplary mention may also be made of the products sold under the names ABIL WAX® 9800 and 9801 by the company Goldschmidt, which are poly($C_1$-$C_{20}$)dialkylsiloxanes.

The silicone gums that can be used in accordance with the disclosure are polydialkylsiloxanes, for instance polydimethylsiloxanes with high number-average molecular masses ranging from 200,000 to 1,000,000, used alone or as a mixture in a solvent. This solvent can be chosen, for example, from volatile silicones, polydimethylsiloxane (PDMS) oils, polyphenylmethylsiloxane (PPMS) oils, isoparaffins, polyisobutylenes, methylene chloride, pentane, dodecane and tridecane, and mixtures thereof.

For example, products that can be used in accordance with the disclosure are mixtures chosen from:

mixtures formed from a polydimethylsiloxane hydroxylated at the chain end, or dimethiconol (CTFA) and from a cyclic polydimethylsiloxane also known as cyclomethicone (CTFA), such as the product Q2 1401 sold by the company Dow Corning;

mixtures formed from a polydimethylsiloxane gum with a cyclic silicone, such as the product SF 1214 SILICONE FLUID from the company General Electric; this product is an SF 30 gum corresponding to a dimethicone, having a number-average molecular weight of 500,000, dissolved in the oil SF 1202 SILICONE FLUID corresponding to decamethylcyclopentasiloxane;

mixtures of two PDMSs with different viscosities, for example of a PDMS gum and a PDMS oil, such as the product SF 1236 from the company General Electric. The product SF 1236 is a mixture of an SE 30 gum defined above, having a viscosity of 20 m$^2$/s, and an SF 96 oil, with a viscosity of $5 \times 10^{-6}$ m$^2$/s. This product may, for example, contain 15% SE 30 gum and 85% SF 96 oil.

The organopolysiloxane resins that can be used in accordance with the disclosure are crosslinked siloxane systems containing the following units:

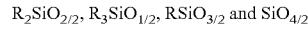

wherein R represents an alkyl containing 1 to 16 carbon atoms. In at least one embodiment, R denotes a $C_1$-$C_4$ lower alkyl radical, and in at least one embodiment, R is methyl.

Among these resins, exemplary mention may be made of the product sold under the name DOW CORNING 593 or those sold under the names SILICONE FLUID SS 4230 and SS 4267 by the company General Electric, which are silicones of dimethyl/trimethyl siloxane structure.

Exemplary mention may also be made of the trimethyl siloxysilicate type resins sold, for example, under the names X22-4914, X21-5034 and X21-5037 by the company Shin-Etsu.

The organomodified silicones that can be used in accordance with the disclosure are silicones as defined above and comprising in their structure at least one organofunctional group attached via a hydrocarbon-based radical.

Besides the silicones described above, the organomodified silicones may be polydiarylsiloxanes, such as polydiphenylsiloxanes, and polyalkylarylsiloxanes functionalized with the organofunctional groups mentioned previously.

The polyalkylarylsiloxanes are chosen, in at least one embodiment, from linear and/or branched polydimethyl/methylphenylsiloxanes and polydimethyl/diphenylsiloxanes with a viscosity ranging from $1 \times 10^{-5}$ to $5 \times 10^{-2}$ m$^2$/s at 25° C.

Among these polyalkylarylsiloxanes, examples that may be mentioned include the products sold under the following names:

the SILBIONE® oils of the 70 641 series from Rhodia;

the oils of the RHODORSIL® 70 633 and 763 series from Rhodia;

the oil DOW CORNING 556 COSMETIC GRADE FLUID from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

Among the organomodified silicones, exemplary mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET® L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 SILICONE FLUID and GP 7100 by the company Genesee, or the products sold under the names Q2 8220 and DOW CORNING 929 or 939 by the company Dow Corning. The substituted amine groups are, for example, $C_1$-$C_4$ aminoalkyl groups;

alkoxylated groups such as the product sold under the name Silicone Copolymer F-755 by SWS Silicones, and ABIL WAX® 2428, 2434 and 2440 by the company Goldschmidt.

In at least one embodiment, the fatty substances do not comprise any $C_2$-$C_3$ oxyalkylene units or any glycerolated units.

In at least one embodiment, the at least one fatty substance is chosen from compounds that are liquid or pasty at room temperature and at atmospheric pressure.

In at least one embodiment, the at least one fatty substance is a compound that is liquid at a temperature of 25° C. and at atmospheric pressure.

In at least one embodiment, the at least one fatty substance is different from the fatty acids.

The at least one fatty substance is, in at least one embodiment, chosen from $C_6$-$C_{16}$ lower alkanes, non-silicone oils of plant, mineral and synthetic origin, fatty alcohols, fatty acid esters, fatty alcohol esters, and silicones, and in at least one embodiment is chosen from $C_6$-$C_{16}$ lower alkanes, non-silicone oils of plant, mineral and synthetic origin, fatty alcohols, fatty acid esters, and fatty alcohol esters.

In some embodiments, the at least one fatty substance is chosen from liquid petroleum jelly, polyethylenes, liquid fatty acid esters, and liquid fatty alcohol esters.

The composition according to the disclosure comprises at least 25% by weight of at least one fatty substance relative to the total weight of the composition. In at least one embodiment, the at least one fatty substance is present in the composition in a total amount ranging from 25% to 80% by weight relative to the total weight of the composition, such as from 25% to 65% or such as from 30% to 55% by weight relative to the total weight of the composition.

The composition according to the disclosure moreover comprises from 0.1% to 15% by weight of at least one silicates relative to the total weight of the composition.

The silicates of the disclosure may, for example, be natural or chemically modified (or synthetic).

Silicates correspond to optionally hydrated silica, some of the silicon atoms of which have been replaced with metal cations such as $Al^{3+}$, $B^{3+}$, $Fe^{3+}$, $Ga^{3+}$, $Be^{2+}$, $Zn^{2+}$, $Mg^{2+}$, $Co^{3+}$, $Ni^{3+}$, $Na^+$, $Li^+$, $C^{2+}$ or $Cu^{2+}$.

In at least one embodiment, the at least one silicate is chosen from:

smectite clays, such as montmorillonites, hectorites, bentonites, beidellites and saponites, and vermiculite, stevensite and chlorite clays.

In at least one embodiment, the at least one silicate is chosen from clays of natural and synthetic origin. In at least one embodiment, clays that are cosmetically compatible and acceptable with keratin materials are used.

In at least one embodiment, the at least one silicate is chosen from montmorillonite, bentonite, hectorite, attapulgite and sepiolite.

Exemplary mention may also be made of the compounds sold by the company Laporte under the brand name LAPONITE XLG and LAPONITE XLS.

In at least one embodiment, the at least one silicate is chosen from bentonite and hectorite.

For example, the at least one silicate may be modified with at least one compound chosen from quaternary amines, tertiary amines, amine acetates, imidazolines, amine soaps, fatty sulfates, alkyl aryl sulfonates and amine oxides.

For example, suitable silicates that may be mentioned include quaternium-18 bentonites such as those sold under the names BENTONE 3, BENTONE 38 and BENTONE 38V by the company Rheox, TIXOGEL VP by the company United Catalyst, CLAYTONE 34, CLAYTONE 40 and CLAYTONE XL by the company Southern Clay; stearalkonium bentonites such as those sold under the names BENTONE 27 by the company Rheox, TIXOGEL LG by the company United Catalyst and CLAYTONE AF and CLAYTONE APA by the company Southern Clay; quaternium-18/benzalkonium bentonites such as those sold under the names CLAYTONE HT and CLAYTONE PS by the company Southern Clay; quaternium-18 hectorites such as those sold under the names BENTONE GEL DOA, BENTONE GEL ECO5, BENTONE GEL EUG, BENTONE GEL IPP, BENTONE GEL ISD, BENTONE GEL SS71, BENTONE GEL VS8 and BENTONE GEL VS38 by the company Rheox, and SIMAGEL M and SIMAGEL SI345 by the company Biophil.

As indicated previously, the composition according to the disclosure comprises at least one silicate in a total amount ranging from 0.15% to 15% by weight relative to the total weight of the composition, such as from 0.5% to 10% by weight relative to the weight of the composition.

The composition according to the disclosure may optionally comprise at least one dye chosen from oxidation dyes and direct dyes.

For example, in at least one embodiment the composition according to the disclosure comprises at least one oxidation dye.

The oxidation dyes may, for example, be chosen from at least one oxidation base optionally combined with at least one coupler.

The oxidation bases may be chosen, for example, from para-phenylenediamines, bis(phenyl)alkylenediamines, para-aminophenols, ortho-aminophenols and heterocyclic bases, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylene-diamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-β-hydroxy-ethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the addition salts thereof with an acid.

Among the para-phenylenediamines mentioned above, para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the addition salts thereof with an acid may, for example, be mentioned.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diamino-phenoxy)-3,6-dioxaoctane, and the addition salts thereof.

Among the para-aminophenols that may be mentioned, for example, are para-aminophenol, 4-amino-3-methylphenol, 4-amino-3-fluorophenol, 4-amino-3-chlorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(β-hydroxyethylaminomethyl)phenol and 4-amino-2-fluorophenol, and the addition salts thereof with an acid.

Among the ortho-aminophenols that may be mentioned, for example, are 2-aminophenol, 2-amino-5-methylphenol, 2-amino-6-methylphenol and 5-acetamido-2-aminophenol, and the addition salts thereof.

Among the heterocyclic bases that may be mentioned, for example, are pyridine derivatives, pyrimidine derivatives and pyrazole derivatives.

Among the pyridine derivatives that may be mentioned are the compounds described, for example, in patents GB 1 026 978 and GB 1 153 196, for instance 2,5-diaminopyridine, 2-(4-methoxyphenyl)amino-3-aminopyridine and 3,4-diaminopyridine, and the addition salts thereof.

Other pyridine oxidation bases that may be useful in the present disclosure include the 3-aminopyrazolo[1,5-a]pyridine oxidation bases or addition salts thereof described, for example, in patent application FR 2 801 308. Examples that may be mentioned include pyrazolo[1,5-a]pyrid-3-ylamine, 2-acetylaminopyrazolo[1,5-a]pyrid-3-ylamine, 2-morpholin-4-ylpyrazolo[1,5-a]pyrid-3-ylamine, 3-aminopyrazolo[1,5-a]pyridine-2-carboxylic acid, 2-methoxypyrazolo[1,5-a]pyrid-3-ylamine, (3-aminopyrazolo[1,5-a]pyrid-7-yl)methanol, 2-(3-aminopyrazolo[1,5-a]pyrid-5-yl)ethanol, 2-(3-aminopyrazolo[1,5-a]pyrid-7-yl)ethanol, (3-aminopyrazolo[1,5-a]pyrid-2-yl)methanol, 3,6-diaminopyrazolo[1,5-a]pyridine, 3,4-diaminopyrazolo[1,5-a]pyridine, pyrazolo[1,5-a]pyridine-3,7-diamine, 7-morpholin-4-ylpyrazolo[1,5-a]pyrid-3-ylamine, pyrazolo[1,5-a]pyridine-3,5-diamine, 5-morpholin-4-yl-pyrazolo[1,5-a]pyrid-3-ylamine, 2-[(3-aminopyrazolo[1,5-a]pyrid-5-yl)(2-hydroxy-ethyl)amino]ethanol, 2-[(3-aminopyrazolo[1,5-a]pyrid-7-yl)(2-hydroxyethyl)amino]ethanol, 3-aminopyrazolo[1,5-a]pyridin-5-ol, 3-aminopyrazolo[1,5-a]pyridin-4-ol, 3-aminopyrazolo[1,5-a]pyridin-6-ol and 3-aminopyrazolo[1,5-a]pyridin-7-ol, and the addition salts thereof.

Among the pyrimidine derivatives that may be mentioned are the compounds described, for example, in patents DE 2 359 399; JP 88-169 571; JP 05-63124; EP 0 770 375 or patent application WO 96/15765, for instance 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and the addition salts thereof, and the tautomeric forms thereof, when a tautomeric equilibrium exists.

Among the pyrazole derivatives that may be mentioned are the compounds described in patents DE 3 843 892 and DE 4 133 957, and patent applications WO 94/08969, WO 94/08970, FR-A-2 733 749 and DE 195 43 988, for instance 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethyl-pyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl)amino-1-methylpyrazole, and the addition salts thereof. In at least one embodiment, 4,5-Diamino-1-(β-methoxyethyl) pyrazole may be used.

In some embodiments, a 4,5-diaminopyrazole is used, and in at least one embodiment, 4,5-diamino-1-(β-hydroxyethyl) pyrazole and/or a salt thereof.

Pyrazoles that may also be mentioned include, for example, diamino-N,N-dihydropyrazolopyrazolones and, for example, those described in patent application FR-A-2 886 136, such as the following compounds and the addition salts thereof: 2,3-diamino-6,7-dihydro-1H,5H-pyrazolo[1,2-a]pyrazol-1-one, 2-amino-3-ethylamino-6,7-dihydro-1H,5H-pyrazolo[1,2-a]pyrazol-1-one, 2-amino-3-isopropylamino-6,7-dihydro-1H,5H-pyrazolo[1,2-a]pyrazol-1-one, 2-amino-3-(pyrrolidin-1-yl)-6,7-dihydro-1H,5H-pyrazolo[1,2-a]pyrazol-1-one, 4,5-diamino-1,2-dimethyl-1,2-dihydropyrazol-3-one, 4,5-diamino-1,2-diethyl-1,2-dihydropyrazol-3-one, 4,5-diamino-1,2-di-(2-hydroxyethyl)-1,2-dihydropyrazol-3-one, 2-amino-3-(2-hydroxyethyl)amino-6,7-dihydro-1H,5H-pyrazolo[1,2-a]pyrazol-1-one, 2-amino-3-dimethylamino-6,7-dihydro-1H,5H-pyrazolo[1,2-a]pyrazol-1-one, 2,3-diamino-5,6,7,8-tetrahydro-1H,6H-pyridazino[1,2-a]pyrazol-1-one, 4-amino-1,2-diethyl-5-(pyrrolidin-1-yl)-1,2-dihydropyrazol-3-one, 4-amino-5-(3-dimethylamino-pyrrolidin-1-yl)-1,2-diethyl-1,2-dihydropyrazol-3-one, and 2,3-diamino-6-hydroxy-6,7-dihydro-1H,5H-pyrazolo[1,2-a]pyrazol-1-one.

In at least one embodiment, 2,3-Diamino-6,7-dihydro-1H,5H-pyrazolo[1,2-a]pyrazol-1-one and/or a salt thereof will be used.

4,5-Diamino-1-(β-hydroxyethyl)pyrazole and/or 2,3-diamino-6,7-dihydro-1H,5H-pyrazolo[1,2-a]pyrazol-1-one and/or a salt thereof is used as heterocyclic base.

The composition according to the disclosure may optionally comprise at least one coupler, that in at least one embodiment is chosen from those conventionally used in the dyeing of keratin fibers.

Among these couplers, exemplary mention may be made of meta-phenylenediamines, meta-aminophenols, meta-diphenols, naphthalene-based couplers and heterocyclic couplers, and the addition salts thereof.

Mention may be made, for example, of 1,3-dihydroxybenzene, 1,3-dihydroxy-2-methylbenzene, 4-chloro-1,3-dihydroxybenzene, 2,4-diamino-1-(β-hydroxy-ethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methyl-indole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, 6-hydroxyindoline, 2,6-dihydroxy-4-methylpyridine, 1-H-3-methylpyrazol-5-one, 1-phenyl-3-methylpyrazol-5-one, 2,6-dimethylpyrazolo[1,5-b]-1,2,4-triazole, 2,6-dimethyl[3,2-c]-1,2,4-triazole and 6-methylpyrazolo[1,5-a]benzimidazole, the addition salts thereof with an acid, and mixtures thereof.

In general, the addition salts of the oxidation bases and couplers that may be used in the context of the disclosure may be, for example, chosen from the addition salts with an acid such as the hydrochlorides, hydrobromides, sulfates, citrates, succinates, tartrates, lactates, tosylates, benzenesulfonates, phosphates and acetates.

In at least one embodiment, the at least one oxidation base is present in a total amount ranging from 0.0001% to 10% by weight relative to the total weight of the composition, such as from 0.005% to 5% by weight relative to the total weight of the composition.

The at least one coupler, if it is present, is present in an amount ranging from 0.0001% to 10% by weight relative to the total weight of the composition, for example from 0.005% to 5% by weight relative to the total weight of the composition.

The composition according to the disclosure may optionally comprise, in addition to the at least one oxidation dye, at least one synthetic or natural direct dye, chosen from ionic and nonionic species, and in at least one embodiment comprises at least one synthetic or natural direct dye chosen from cationic or nonionic species.

As examples of direct dyes that are suitable for use, exemplary mention may be made of azo; methine; carbonyl; azine; nitro (hetero)aryl; tri(hetero)arylmethane; porphyrin; phthalocyanine direct dyes; and natural direct dyes, alone or as mixtures.

Among the natural direct dyes that may be used according to the disclosure, exemplary mention may be made of lawsone, juglone, alizarin, purpurin, carminic acid, kermesic acid, purpurogallin, protocatechaldehyde, indigo, isatin, curcumin, spinulosin, apigenidin and orceins. It is also possible, for example, to use extracts or decoctions containing these natural dyes, such as henna-based poultices or extracts.

When present, in at least one embodiment, the at least one direct dye is present in a total amount ranging from 0.0001% to 10% by weight relative to the total weight of the composition, such as from 0.005% to 5% by weight relative to the total weight of the composition.

The composition according to the disclosure also comprises at least one oxidizing agent.

In at least one embodiment, the at least one oxidizing agent is chosen from hydrogen peroxide, urea peroxide, alkali metal bromates or ferricyanides, peroxygenated salts, for instance alkali metal or alkaline-earth persulfates, perborates and percarbonates, and also peracids and precursors thereof.

In at least one embodiment, the oxidizing agent is not chosen from peroxygenated salts.

In at least one embodiment, the oxidizing agent is hydrogen peroxide.

In at least one embodiment, the at least one oxidizing agent is present in an amount ranging from 0.1% to 20% by weight relative to the total weight of the composition, such as from 0.5% to 10% by weight relative to the total weight of the composition.

The at least one basifying agent may, for example, be mineral or organic or hybrid.

The at least one mineral basifying agent is chosen, in some embodiments, from aqueous ammonia, alkali metal carbonates or bicarbonates such as sodium carbonate or potassium carbonate and sodium bicarbonate or potassium bicarbonate, sodium hydroxide and potassium hydroxide.

The at least one organic basifying agent can be chosen from organic amines whose pKb at 25° C. is less than 12, such as less than 10 or such as less than 6. It should be noted that it is the pKb corresponding to the function of highest basicity.

The at least one organic basifying agent is chosen, for example, from alkanolamines, oxyethylenated and/or oxypropylenated ethylenediamines, amino acids and the compounds of formula (IX) below:

(IX)

wherein W is a $C_1$-$C_6$ alkylene residue optionally substituted with a hydroxyl group or a $C_1$-$C_6$ alkyl radical; Rx, Ry, Rz and Rt, which may be identical or different, represent a hydrogen atom or a $C_1$-$C_6$ alkyl, $C_1$-$C_6$ hydroxyalkyl or $C_1$-$C_6$ aminoalkyl radical, are also suitable for use.

Examples of such amines that may be mentioned include 1,3-diaminopropane, 1,3-diamino-2-propanol, spermine and spermidine.

The term "alkanolamine" means an organic amine comprising a primary, secondary or tertiary amine function, and at least one linear or branched $C_1$-$C_8$ alkyl group bearing at least one hydroxyl radical.

Alkanolamines such as mono-, di- or tri-alkanolamines comprising from one to three identical or different $C_1$-$C_4$ hydroxyalkyl radicals are, for example, suitable for the disclosure.

Among the compounds of this type, exemplary mention may be made of monoethanolamine, diethanolamine, triethanolamine, monoisopropanolamine, diisopropanolamine, N-dimethylaminoethanolamine, 2-amino-2-methyl-1-propanol, triisopropanolamine, 2-amino-2-methyl-1,3-propanediol, 3-amino-1,2-propanediol, 3-dimethylamino-1,2-propanediol and tris(hydroxymethylamino)methane.

For example, the amino acids that may be used may be of natural or synthetic origin, in L, D or racemic form, and may comprise at least one acid function chosen, for example, from carboxylic acid, sulfonic acid, phosphonic acid and phosphoric acid functions. The amino acids may be in their neutral or ionic form.

As amino acids that may be used in the present disclosure, exemplary mention may be made of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

For example, the amino acids can be basic amino acids comprising an additional amine function optionally included in a ring or in a ureido function.

Such basic amino acids are in at least one embodiment chosen from those of formula (X):

$$R-CH_2-CH\begin{matrix}NH_2\\CO_2H\end{matrix} \quad (X)$$

wherein R denotes a group chosen from:

imidazolyl; —$(CH_2)_3NH_2$; —$(CH_2)_2NH_2$;

—$(CH_2)_2NHCONH_2$; and —$(CH_2)_2NH-\underset{\underset{NH}{\|}}{C}-NH_2$.

The compounds corresponding to formula (X) are histidine, lysine, arginine, ornithine and citrulline.

The organic amine may also be chosen, for example, from heterocyclic organic amines. Besides histidine that has already been mentioned in the amino acids, mention may be made, for example, of pyridine, piperidine, imidazole, triazole, tetrazole and benzimidazole.

For example, the organic amine may be chosen from amino acid dipeptides. As amino acid dipeptides that may be used in the present disclosure, mention may be made, for example, of carnosine, anserine and baleine.

In at least one embodiment, the organic amine is chosen from compounds comprising a guanidine function. As amines of this type that may be used in the present disclosure, besides arginine that has already been mentioned as an amino acid, exemplary mention may be made of creatine, creatinine, 1,1-dimethylguanidine, 1,1-diethylguanidine, glycocyamine, metformin, agmatine, N-amidinoalanine, 3-guanidinopropionic acid, 4-guanidinobutyric acid and 2-([amino(imino)methyl]amino)ethane-1-sulfonic acid.

In at least one embodiment, the organic amine present in the composition of the disclosure is an alkanolamine.

In at least one embodiment, the organic amine is monoethanolamine.

Hybrid compounds that may be mentioned, for example, include salts of the amines mentioned previously with acids such as carbonic acid or hydrochloric acid.

In some embodiments, guanidine carbonate or monoethanolamine hydrochloride may be used.

In at least one embodiment, the composition according to the disclosure comprises at least one basifying agent in an amount ranging from 0.01% to 30% by weight relative to the total weight of the composition, such as from 0.1% to 20% by weight relative to the weight of the composition.

In at least one embodiment, the composition according to the disclosure does not comprise any aqueous ammonia or one of its salts, as basifying agent. If, however, it did contain any, the aqueous ammonia or salt of aqueous ammonia would be present in an amount of less than 0.03% by weight (expressed as $NH_3$) relative to the total weight of the composition, for example less than 0.01% by weight relative to the weight of the composition according to the disclosure. In at least one embodiment, if the composition comprises aqueous ammonia or one of its salts, then the at least one basifying agent is present in an amount greater than the amount of aqueous ammonia (expressed as $NH_3$).

For example, the composition of the disclosure may contain at least one alkanolamine and/or at least one basic amino acid.

In at least one embodiment, the composition of the disclosure comprises monoethanolamine.

The composition according to the disclosure may also comprise at least one surfactant.

In at least one embodiment, the at least one surfactant is chosen from nonionic surfactants and anionic surfactants.

In at least one embodiment, the at least one anionic surfactant is chosen from the salts (for example alkali metal salts, such as sodium salts, ammonium salts, amine salts, amino alcohol salts or alkaline-earth metal salts such as magnesium salts) of:

alkyl sulfates, alkyl ether sulfates, alkylamido ether sulfates, alkylaryl polyether sulfates, monoglyceride sulfates;

alkylsulfonates, alkylamidesulfonates, alkylarylsulfonates, α-olefin sulfonates, paraffin sulfonates;

alkyl phosphates, alkyl ether phosphates;

alkylsulfosuccinates, alkyl ether sulfosuccinates, alkylamidesulfosuccinates;

alkylsulfosuccinamates;

alkylsulfoacetates;

acylsarcosinates; acylisethionates and N-acyltaurates;

fatty acids such as oleic acid, ricinoleic acid, palmitic acid or stearic acid, coconut oil acid or hydrogenated coconut oil acid;

alkyl-D-galactoside uronic acid;

acyllactylates; and polyoxyalkylenated alkyl ether carboxylic acids, polyoxyalkylenated alkylaryl ether carboxylic acids and polyoxyalkylenated alkylamido ether carboxylic acids, for instance those containing from 2 to 50 ethylene oxide groups.

It should be noted that the alkyl or acyl radical of these various compounds may, for example, contain from 6 to 24 carbon atoms such as from 8 to 24 carbon atoms, and the aryl radical, in at least one embodiment, denotes a phenyl or benzyl group.

In some embodiments, the at least one nonionic surfactant is chosen from monooxyalkylenated and polyoxyalkylenated, monoglycerolated and polyglycerolated nonionic surfactants. The oxyalkylene units are, in at least one embodiment, chosen from oxyethylene and oxypropylene units, and combinations thereof, such as oxyethylene units.

Examples of oxyalkylenated nonionic surfactants that may be mentioned include:

oxyalkylenated ($C_8$-$C_{24}$)alkylphenols, saturated and unsaturated, linear and branched, oxyalkylenated $C_8$-$C_{30}$ alcohols, saturated and unsaturated, linear and branched, oxyalkylenated $C_8$-$C_{30}$ amides, saturated and unsaturated, linear and branched, $C_8$-$C_{30}$ acid esters and polyethylene glycol esters, saturated and unsaturated, linear and branched, polyoxyethylenated $C_8$-$C_{30}$ acid esters and polyoxyethylenated sorbitol esters, saturated or unsaturated, oxyethylenated plant oils, and condensates of ethylene oxide and/or of propylene oxide, alone or as mixtures.

The at least one surfactant comprises ethylene oxide and/or propylene oxide in an amount ranging from 1 to 100 mol, for example from 2 to 50 mol or for example from 2 to 30 mol. In at least one embodiment, the at least one nonionic surfactant does not comprise any oxypropylene units.

In accordance with some embodiments of the disclosure, the oxyalkylenated nonionic surfactants are chosen from oxyethylenated $C_8$-$C_{30}$ alcohols comprising ethylene oxide in an amount ranging from 1 to 100 mol; and polyoxyethylenated linear and branched, saturated and unsaturated $C_8$-$C_{30}$ acid esters and sorbitol esters comprising ethylene oxide in an amount ranging from 1 to 100 mol.

As examples of monoglycerolated or polyglycerolated nonionic surfactants, monoglycerolated or polyglycerolated $C_8$-$C_{40}$ alcohols may be used.

In at least one embodiment, the monoglycerolated or polyglycerolated $C_8$-$C_{40}$ alcohols correspond to the following formula:

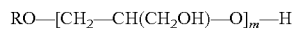
RO—[CH$_2$—CH(CH$_2$OH)—O]$_m$—H wherein R represents a linear or branched $C_8$-$C_{40}$, such as $C_8$-$C_{30}$, alkyl or alkenyl radical, and m represents a number ranging from 1 to 30, for example from 1 to 10.

As examples of compounds that are suitable in the context of the disclosure, mention may be made of lauryl alcohol containing 4 mol of glycerol (INCI name: Polyglyceryl-4 Lauryl Ether), lauryl alcohol containing 1.5 mol of glycerol, oleyl alcohol containing 4 mol of glycerol (INCI name: Polyglyceryl-4 Oleyl Ether), oleyl alcohol containing 2 mol of glycerol (INCI name: Polyglyceryl-2 Oleyl Ether), cetearyl alcohol containing 2 mol of glycerol, cetearyl alcohol containing 6 mol of glycerol, oleocetyl alcohol containing 6 mol of glycerol, and octadecanol containing 6 mol of glycerol.

The alcohol may represent a mixture of alcohols in the same way that the value of m represents a statistical value, which means that, in a commercial product, several species of polyglycerolated fatty alcohol may coexist in the form of a mixture.

In at least one embodiment, the monoglycerolated or polyglycerolated alcohols are chosen from $C_8$/$C_{10}$ alcohols containing 1 mol of glycerol, $C_{10}$/$C_{12}$ alcohols containing 1 mol of glycerol and s $C_{12}$ alcohols containing 1.5 mol of glycerol.

In at least one embodiment, the at least one surfactant present in the composition is a nonionic surfactant.

For example, the at least one surfactant is present in the composition in a total amount ranging from 0.1% to 50% by weight relative to the total weight of the composition, such as from 0.5% to 30% by weight relative to the total weight of the composition.

The composition may also, for example, contain various adjuvants conventionally used in hair dye compositions, such as anionic, cationic, nonionic, amphoteric or zwitterionic polymers or mixtures thereof; antioxidants; penetrants; sequestrants; fragrances; dispersants; film-forming agents; ceramides; preserving agents; opacifiers.

The above adjuvants may, for example, be present in an amount for each of them ranging from 0.01% to 20% by weight relative to the total weight of the composition.

For example, the composition may comprise at least one fumed silica.

The at least one fumed silica may be obtained by high-temperature hydrolysis of a volatile silicon compound in an oxhydric flame, producing a finely divided silica. This process may make it possible, for example, to obtain hydrophilic silicas having a large number of silanol groups at their surface. Such hydrophilic silicas are sold, for example, under the names AEROSIL 130®, AEROSIL 200®, AEROSIL 255®, AEROSIL 300® and AEROSIL 380® by the company Degussa, and CAB-O-SIL HS-5®, CAB-O-SIL EH-5®, CAB-O-SIL LM-130®, CAB-O-SIL MS-55® and CAB-O-SIL M-5® by the company Cabot.

It is possible to chemically modify the surface of the ilica, via a chemical reaction generating a reduction in the number of silanol groups. It is, for example, possible to substitute silanol groups with hydrophobic groups: a hydrophobic silica is then obtained.

The hydrophobic groups may be, for example:

trimethylsiloxyl groups, which are obtained especially by treating fumed silica in the presence of hexamethyldisilazane. Silicas thus treated are known as "silica silylate" according to the CTFA (6th Edition, 1995). They are sold, for example, under the references AEROSIL R812® by the company Degussa and CAB-O-SIL TS-530® by the company Cabot;

dimethylsilyloxyl or polydimethylsiloxane groups, which are obtained, for example, by treating fumed silica in the presence of polydimethylsiloxane or dimethyldichlorosilane. Silicas thus treated are known as "silica dimethyl silylate" according to the CTFA (6th Edition, 1995). They are sold, for example, under the references AEROSIL R972® and AEROSIL R974® by the company Degussa and CAB-O-SIL TS-610 ® and CAB-O-SIL TS-720® by the company Cabot.

In at least one embodiment, he at least one fumed silica has a particle size ranging from nanometric to micrometric, for example ranging from 5 to 200 nm.

When it is present, the at least one fumed silica is present in an amount ranging from 1% to 30% by weight relative to the weight of the composition.

The composition may also comprise at least one organic thickener.

These thickeners may, for example, be chosen from fatty acid amides (coconut monoethanolamide or diethanolamide, oxyethylenated carboxylic acid monoethanolamide alkyl ether), polymeric thickeners such as cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum), acrylic acid or acrylamidopropane-sulfonic acid crosslinked homopolymers and associative polymers (polymers comprising hydrophilic regions and fatty-chain hydrophobic regions (alkyl or alkenyl containing at least 10 carbon atoms) that are capable, in an aqueous medium, of reversibly combining with each other or with other molecules).

According to one embodiment, the at least one organic thickener is chosen from cellulose-based thickeners (hydroxyethylcellulose, hydroxypropylcellulose or carboxymethylcellulose), guar gum and derivatives thereof (hydroxypropyl guar), gums of microbial origin (xanthan gum, scleroglucan gum) and acrylic acid or acrylamidopropane-sulfonic acid crosslinked homopolymers, for example from cellulose-based thickeners, for instance with hydroxyethylcellulose.

The at least one organic thickener, if present, may be present in an amount ranging from 0.01% to 20% by weight relative to the total weight of the composition, such as from 0.1% to 5% by weight relative to the weight of the composition.

The cosmetically acceptable medium of the composition according to the disclosure is a medium comprising water and optionally at least one organic solvent.

Examples of organic solvents that may be mentioned include linear or branched and preferably saturated monoalcohols or diols, containing 2 to 10 carbon atoms, such as ethyl alcohol, isopropyl alcohol, hexylene glycol (2-methyl-2,4-pentanediol), neopentyl glycol and 3-methyl-1,5-pentanediol; aromatic alcohols such as benzyl alcohol and phenylethyl alcohol; glycerol; polyols or polyol ethers, for instance ethylene glycol monomethyl, monoethyl and monobutyl ethers, 2-butoxyethanol, propylene glycol or ethers thereof, for instance propylene glycol, butylene glycol or dipropylene glycol monomethyl ether; and also diethylene glycol alkyl ethers, for example $C_1$-$C_4$ ethers, for instance diethylene glycol monoethyl ether or monobutyl ether, alone or as a mixture.

The solvents, when they are present, may be present in an amount ranging from 1% to 40% by weight relative to the total weight of the dye composition, for example from 5% to 30% by weight relative to the total weight of the dye composition.

In at least one embodiment, the composition of the disclosure contains water.

For example, the water may be present in an amount ranging from 10% to 70% by weight relative to the total weight of the composition, such as from 20% to 55% by weight relative to the total weight of the composition.

The dye composition according to the disclosure may be in various forms, such as in the form of liquids, creams or gels, or in any other form that is suitable for dyeing keratin fibers, such as human hair.

In at least one embodiment, the composition according to the disclosure is in the form of a gel or a cream.

For example, the pH of the composition according to the disclosure may range from 3 to 12, such as from 5 to 11, or from 7 to 11, limits inclusive.

It may be adjusted to the desired value via acidifying or basifying agents usually used in the dyeing of keratin fibers, or alternatively using standard buffer systems.

The alkaline agents include, for example, those described previously.

Examples of acidifying agents that may be mentioned include mineral or organic acids, for instance hydrochloric acid, orthophosphoric acid, carboxylic acids, for instance tartaric acid, citric acid or lactic acid, or sulfonic acids.

The composition of the disclosure may be obtained by mixing at least two or at least three different compositions, or optionally more than three different compositions. For example, at least one of the compositions leading, by mixing, to the composition of the disclosure may be anhydrous.

Anhydrous composition means, in the sense of the disclosure, a composition comprising water in an amount ranging from 0% to 5% by weight relative to the total weight of the composition, for example less than 2% or for example less than 1% by weight relative to the total weight of the composition. It should be noted that the water can also be in the form of bound water, such as the water of crystallization of salts or traces of water absorbed by the raw materials used in the preparation of the compositions according to the disclosure.

It should be noted that the composition according to the disclosure is prepared just before being applied to the human keratin fibers.

In at least one embodiment, the composition according to the disclosure is obtained by mixing
- at least one first composition comprising at least one fatty substance, at least one silicate and optionally at least one dye; and
- at least one second composition comprising at least one oxidizing agent;
- wherein at least one basifying agent is optionally present in one of the compositions, and in at least one embodiment is present in the first composition;
- and the at least one silicate is present in a total amount ranging from 0.1% to 15% by weight relative to the total weight of the composition.

According to one embodiment, the composition according to the disclosure is obtained by mixing
- at least one first composition comprising at least one fatty substance, at least one silicate and at least one oxidation dye; and
- at least one second composition comprising at least one oxidizing agent;
- wherein at least one basifying agent is optionally present in either composition, and in at least one embodiment is present in the first composition; and the at least one silicate is present in a total amount ranging from 0.1% to 15% by weight relative to the total weight of the composition.

According to at least one embodiment of the disclosure, the composition according to the disclosure is obtained by mixing
- at least one first composition comprising at least one fatty substance and at least one silicate;
- at least one second composition comprising at least one dye and at least one basifying agent; and
- at least one third composition comprising at least one oxidizing agent;
- wherein the at least one silicate is present in a total amount ranging from 0.1% to 15% by weight relative to the total weight of the composition.

The first composition may in some embodiments be anhydrous.

For example, it should be noted that if the composition does not comprise at least one dye, the at least one basifying agent is in the at least one second composition.

If the composition comprises at least one dye, then at least one basifying agent is optionally present in at least one of the three abovementioned compositions, and in at least one embodiment is present in the first composition.

According to at least one additional embodiment of the disclosure, the composition according to the disclosure is obtained by mixing a first composition comprising at least one fatty substance and at least one silicate, a second composition comprising at least one oxidation dye and a third composition comprising at least one oxidizing agent; wherein at least one basifying agent is optionally present in either of the abovementioned compositions and in some embodiments is present in the first and/or second composition; and wherein the at least one silicate is present in a total amount ranging from 0.1% to 15% by weight relative to the total weight of the composition. In at least one embodiment, the first composition may be anhydrous.

The ingredients of the abovementioned compositions and the contents thereof are determined as a function of the characteristics detailed previously for the final composition according to the disclosure.

In some embodiments, the at least one oxidizing composition is an aqueous composition. In at least one embodiment, it comprises water in an amount of at least 5% by weight relative to the total weight of the composition, for example in an amount of at least 10% by weight, or for example at least 20% by weight.

For example, it may also optionally comprise at least one organic solvent chosen from those listed previously. In at least one embodiment the at least one solvent is present in an amount ranging from 1% to 40% by weight relative to the total weight of the oxidizing composition, such as from 5% to 30% by weight relative to the weight of the oxidizing composition.

In at least one embodiment, the oxidizing composition also comprises at least one acidifying agent. Among acidifying agents, examples that may be mentioned include mineral or organic acids, for instance hydrochloric acid, orthophosphoric acid, sulfuric acid, carboxylic acids, for instance acetic acid, tartaric acid, citric acid or lactic acid, and sulfonic acids.

For example, the pH of the oxidizing composition, when it is aqueous, may be less than 7.

In at least one embodiment, the oxidizing composition comprises hydrogen peroxide as oxidizing agent, in aqueous solution, the concentration of which ranges from 0.1% to 50% by weight relative to the total weight of the oxidizing composition, for example from 0.5% to 20% by weight or for example from 1% to 15% by weight relative to the total weight of the oxidizing composition.

The dyeing or lightening process according to the disclosure thus comprises applying the composition according to the disclosure to wet or dry human keratin fibers.

The composition may be then left in place for a time ranging, for example, from one minute to one hour, such as from 5 minutes to 30 minutes.

The temperature during the process may range from room temperature (ranging from 15 to 25° C.) to 80° C., such as from room temperature to 60° C.

After the treatment, the human keratin fibers are optionally rinsed with water, optionally washed with a shampoo and then rinsed with water, before being dried or left to dry.

Another aspect of the disclosure is a multi-compartment device or kit comprising:
at least one compartment containing a first composition comprising at least one fatty substance; and optionally at least one dye chosen from oxidation dyes and direct dyes; and
at least one compartment containing a second composition comprising at least one oxidizing agent;
wherein at least one silicate chosen from smectite, vermiculite, stevensite and chlorite clays is present in at least one of the compositions, and in some embodiments is present in the first composition; and at least one basifying agent is optionally present in at least one of the compositions, and in some embodiments is present in the first composition;
the compositions of the compartments being intended to be mixed together to give the composition according to the disclosure, just before application to the human keratin fibers, such that the composition resulting from the mixing is as defined previously, wherein in at least one embodiment the at least one silicate is present in a total amount ranging from 0.1% to 15% by weight relative to the total weight of the composition.

The disclosure also relates to a multi-compartment device or kit comprising, at least one compartment containing a first composition comprising at least one fatty substance and at least one oxidation dye; and
at least one compartment containing a second composition comprising at least one oxidizing agent;
wherein the at least one silicate is present in at least one of the compositions, and at least one basifying agent is optionally present in either composition, and in some embodiments is present in the first composition; the compositions of the compartments being intended to be mixed together to give the composition according to the disclosure, just before application to the human keratin fibers, such that the composition resulting from the mixing is as defined previously, wherein, in at least one embodiment, the at least one silicate is present in a total amount ranging from 0.1% to 15% by weight relative to the total weight of the composition.

The disclosure furthermore relates to a multi-compartment device or kit comprising:
at least one compartment containing a first composition comprising at least one fatty substance;
at least one compartment containing a second composition comprising at least one dye chosen from oxidation dyes and direct dyes; and at least one basifying agent; and
at least one compartment containing a third composition comprising at least one oxidizing agent;
wherein at least one silicate chosen from smectite, vermiculite, stevensite and chlorite clays is present in at least one of the compositions, and in some embodiments is present in the first composition;
the compositions of the compartments being intended to be mixed together to give the composition according to the disclosure, just before application to human keratin fibers, such that the composition resulting from the mixing is as defined previously, wherein in at least one embodiment, the at least one silicate is present in a total amount ranging from 0.1% to 15% by weight relative to the total weight of the composition.

The disclosure also relates to a multi-compartment device or kit comprising,
at least one compartment containing a first composition comprising at least one fatty substance,
at least one compartment containing a second composition comprising at least one oxidation dye, and
at least one compartment containing a third composition comprising at least one oxidizing agent;
wherein at least one silicate is present in at least one of the compositions, and at least one basifying agent is optionally present in one of the compositions, and in at least one embodiment the at least one silicate and optionally the at least one basifying agent is present in the first or second composition;
the compositions of the compartments being intended to be mixed together to give the composition according to the disclosure, just before application to the human keratin fibers, such that the composition resulting from the mixing is as defined previously, such that the at least one silicate is present in a total amount ranging from 0.1% to 15% by weight relative to the total weight of the composition.

Notwithstanding that the numerical ranges and parameters setting forth the broad scope of the disclosure are approximations, unless otherwise indicated the numerical values set forth in the specific examples are reported as precisely as possible. Any numerical value, however, inherently contains certain errors necessarily resulting from the standard deviation found in their respective testing measurements. By way of non-limiting illustration, concrete examples of certain embodiments of the present disclosure are given below.

The examples that follow serve to illustrate the invention without, however, being limiting in nature.

EXAMPLE 1

The following compositions were prepared (the amounts are expressed in g % of active materials):

Composition 1

| | |
|---|---|
| Disteardimonium hectorite (BENTONE 38 VCG) | 3 |
| Octyldodecanol | 11.5 |
| Glycol distearate | 8 |
| Liquid petroleum jelly | 64.5 |
| Propylene carbonate | 1 |
| Laureth-2 | 1 |
| Polysorbate 21 | 11 |

Composition 2

| | |
|---|---|
| Pentasodium pentetate | 1 |
| Sodium meta bisulfite | 0.7 |
| Monoethanolamine | 14.5 |
| 2,5-Toluenediamine | 2.25 |
| 2,4-Diaminophenoxyethanol hydrochloride | 0.05 |
| Resorcinol | 2 |
| m-Aminophenol | 0.36 |
| Hydroxyethylcellulose (Natrosol 250 HHR, Aqualon) | 1.5 |
| Hexylene glycol | 3 |
| Dipropylene glycol | 3 |
| Ethanol | 8.25 |
| Propylene glycol | 6.2 |
| Ascorbic acid | 0.25 |
| Water | qs 100 |

Composition 3

| | |
|---|---|
| Pentasodium pentetate | 0.15 |
| Hydrogen peroxide (aqueous 50% solution) | 12 |
| Sodium stannate | 0.04 |
| Phosphoric acid | qs pH 2.2 |
| Tetrasodium pyrophosphate | 0.03 |
| Liquid petroleum jelly | 20 |
| Tetramethyl hexamethylenediamine/1,3-dichloro-propylene polycondensate (aqueous 40% solution; Hexadimethrine chloride) | 0.1 |
| Polydimethyldiallylammonium chloride (non-stabilized aqueous 40% solution, Polyquaternium-6) | 0.2 |
| Glycerol | 0.5 |
| Cetylstearyl alcohol (C16/C18 30/70 - Nafol 1618F) | 8 |
| Oxyethylenated cetylstearyl alcohol (33 EO) | 3 |
| Oxyethylenated rapeseed fatty amide (4 EO) | 1.2 |
| Vitamin E: DL-α-tocopherol | 0.1 |
| Water | qs 100 |

Mode of Application

The three compositions detailed above were mixed together at the time of use in the following proportions:
- 10 g of composition 1,
- 4 g of composition 2,
- 16 g of composition 3.

The resulting mixture was then applied to locks of natural hair containing 90% grey hairs, at a rate of 10 g of mixture per 1 g of hair.

The mixture was left on at room temperature for 30 minutes.

The hair was then rinsed, washed with a standard shampoo and dried.

Light-chestnut locks were obtained (visual evaluation).

COMPARATIVE EXAMPLE 2

The following compositions were prepared (the amounts are expressed in g % of active materials):

Compositions A1 and A2

| | A1 (comparative) | A2 (inventive) |
|---|---|---|
| Sodium Metasilicate | 3 | — |
| Disteardimonium hectorite | — | 3 |
| Propylene carbonate | 1 | 1 |
| Octyldodecanol | 11.5 | 11.5 |
| Liquid petroleum jelly | 64.5 | 64.5 |
| Ethylene glycol Distearate | 8 | 8 |
| Laureth-2 | 1 | 1 |
| Oxyethylenated sorbitan monolaurate (4 EO) | 11 | 11 |

Composition B (in grams):

| | |
|---|---|
| p-aminophenol | 1.5805 |
| Amino-3 chloro-2 methyl-6 phenol | 2.2852 |
| Hydroxyethylcellulose (Natrosol 250 HHR) | 1.5 |
| Dipropylene glycol | 3 |
| Hexylene glycol | 3 |
| Propylene glycol | 6.2 |
| Monoethanolamine | 15.04 |
| Ethyl alcohol | 8.25 |
| Reducing agents, sequestering agents | qs |
| Water | Qs 100 |

Composition C (in grams):

| | |
|---|---|
| Hydrogen peroxyde | 6 |
| Cetearyl alcohol | 2.28 |
| Ceteareth-25 | 0.57 |
| Trideceth-2 carboxamide MEA | 0.85 |
| Glycerin | 0.5 |
| Stabilising agents, sequestering | Qs |
| Phosphoric acid | Qs pH = 2 |
| Water | Qs 100 |

At the time of use, 10 g of composition A1 or A2, 4 g of composition B and 15 g of composition C were mixed. In both cases, the pH of the mixture was 9.9±0.1.

The viscosity of each of the mixtures was measured with a Rheomat RM180 rheometer, at 25° C. (rotation speed of 200 rds/mn, mobile 3).

| | A1 + B + C | A2 + B + C (invention) |
|---|---|---|
| Viscosity (mPa · s) | 850 | 1660 |

The viscosity of the mixture obtained with composition A2 is was higher than the viscosity of the mixture obtained with composition A1; which means that the mixture remained where applied, without running out.

Each mixture was then applied onto locks of moderately sensibilized hair (alkaline solubility=27), with 14.5 g of mixture per 1 g of hair.

Each mixture was left on at ambient temperature for 35 minutes.

The hair was then rinsed, washed with a standard shampoo and dried.

The color measures were made with a DATACOLOR SF600X SPECTRAFLASH colorimeter (illuminant D65, angle 10°, specular components included).

Chromaticity

| Mixture | a* | b* | C* |
|---|---|---|---|
| A1 + B + C (comparative) | 23.33 | 21.88 | 31.99 |
| A2 + B + C (inventive) | 23.36 | 25.30 | 34.43 |

It can be seen that the mixture obtained with composition A2 according to the invention yielded a more chromatic color than the mixture with composition A1 outside the scope of the disclosure.

What is claimed is:

1. A composition for dyeing or lightening human keratin fibers, comprising:
   a cosmetically acceptable medium;
   at least 25% by weight of at least one fatty substance;
   from 0.1% to 15% by weight of at least one silicate chosen from smectite, vermiculite, stevensite and chlorite clays;
   at least one dye chosen from oxidation dyes and direct dyes;
   at least one basifying agent; and
   at least one oxidizing agent.

2. The composition according to claim 1, wherein the at least one fatty substance is chosen from $C_6$-$C_{16}$ lower alkanes, non-silicone oils of animal, plant, mineral and synthetic origin, fatty alcohols, fatty acid esters, fatty alcohol esters, non-silicone waxes and silicones.

3. The composition according to claim 1, wherein the at least one fatty substance is chosen from compounds that are liquid or pasty at room temperature and at atmospheric pressure.

4. The composition according to claim 1, wherein the at least one fatty substance is chosen from $C_6$-$C_{16}$ lower alkanes, non-silicone oils of plant, mineral and synthetic origin, fatty alcohols, fatty acid esters and fatty alcohol esters.

5. The composition according to claim 1, wherein the at least one fatty substance is present in a total amount ranging from 25% to 80% by weight relative to the total weight of the composition.

6. The composition according to claim 1, wherein the at least one silicate is a smectite clay chosen from montmorillonites, hectorites, bentonites, beidellites and saponites.

7. The composition according to claim 1, wherein the at least one silicate is modified with at least one compound chosen from quaternary amines, tertiary amines, amine acetates, imidazolines, amine soaps, fatty sulfates, alkyl aryl sulfonates and amine oxides.

8. The composition according to claim 6, wherein the at least one silicate is chosen from quaternium-18 bentonites, stearalkonium bentonites, quaternium-18/benzalkonium bentonites and quaternium-18 hectorites.

9. The composition according to claim 1, wherein the at least one silicate is present in a total amount ranging from 0.5% to 10% by weight relative to the total weight of the composition.

10. The composition according to claim 1, wherein the at least one oxidation dye is chosen from para-phenylenediamines, bis(phenyl)alkylenediamines, para-aminophenols, ortho-aminophenols, heterocyclic bases, and the addition salts thereof.

11. The composition according to claim 10, further comprising at least one coupler chosen from meta-phenylenediamines, meta-aminophenols, meta-diphenols, naphthalene-based couplers, heterocyclic couplers, and the addition salts thereof.

12. The composition according to claim 1, wherein the at least one direct dye is chosen from ionic and nonionic azo dyes; methine dyes; carbonyl dyes; azine dyes; nitro (hetero) aryl dyes; tri(hetero)arylmethane dyes; porphyrin dyes; phthalocyanine dyes; and natural direct dyes.

13. The composition according to claim 1, wherein the at least one basifying agent is chosen from aqueous ammonia, alkali metal carbonates and bicarbonates, sodium hydroxide, potassium hydroxide and organic amines whose pKb at 25° C. is less than 12.

14. The composition according to claim 13, wherein the at least one basifying agent is an organic amine chosen from alkanolamines.

15. The composition according to claim 13, wherein the at least one basifying agent is an organic amine chosen from basic amino acids.

16. A process for dyeing human keratin fibers, comprising applying to keratin fibers a composition comprising:
   a cosmetically acceptable medium;
   at least 25% by weight of at least one fatty substance;
   from 0.1% to 15% by weight of at least one silicate chosen from smectite, vermiculite, stevensite and chlorite clays;
   at least one dye chosen from oxidation dyes and direct dyes;
   at least one basifying agent; and
   at least one oxidizing agent.

17. A multi-compartment kit comprising,
   at least one compartment containing a first composition comprising at least one fatty substance; and
   at least one compartment containing a second composition comprising at least one oxidizing agent;
   wherein at least one silicate chosen from smectite, vermiculite, stevensite and chlorite clays is present in at least one of the compositions, and at least one basifying agent is optionally present in either composition, and at least one dye chosen from oxidation dyes and direct dyes is optionally present in the first composition;
   and further wherein when the compositions of the kit are combined, the at least one fatty substance is present in a total amount of at least 25% by weight relative to the total weight of the combined compositions; and the at least one silicate is present in a total amount ranging from 0.1% to 15% by weight relative to the total weight of the combined compositions.

18. A multi-compartment kit comprising, at least one compartment containing a composition comprising at least one fatty substance, at least one compartment containing a composition comprising at least one dye chosen from oxidation dyes and direct dyes; and at least one basifying agent; and at least one compartment containing a composition comprising at least one oxidizing agent;

wherein at least one silicate chosen from smectite, vermiculite, stevensite and chlorite clays is present in at least one of the compositions;

and further wherein when the compositions of the kit are combined, the at least one fatty substance is present in a total amount of at least 25% by weight relative to the total weight of the combined compositions; and the at least one silicate is present in a total amount ranging from 0.1% to 15% by weight relative to the total weight of the combined compositions.

19. The composition according to claim 3, wherein the at least one fatty substance is chosen from compounds that are liquid at room temperature and at atmospheric pressure.

20. The composition according to claim 5, wherein the at least one fatty substance is present in a total amount ranging from 25% to 65% by weight relative to the total weight of the composition.

21. The composition according to claim 20, wherein the at least one fatty substance is present in a total amount ranging from 30% to 55% by weight relative to the total weight of the composition.

22. The composition according to claim 13, wherein the at least one basifying agent is chosen from organic amines whose pKb at 25° C. is less than 10.

23. The composition according to claim 22, wherein the at least one basifying agent is chosen from organic amines whose pKb at 25° C. is less than 6.

24. The composition according to claim 14, wherein the at least one basifying agent is monoethanolamine.

25. The multi-compartment kit according to claim 17, wherein the at least one silicate is present in the first composition.

26. The multi-compartment kit according to claim 17, wherein the at least one basifying agent is present in the first composition.

* * * * *